United States Patent [19]

Trambert

[11] Patent Number: 5,259,847
[45] Date of Patent: Nov. 9, 1993

[54] CATHETER TO MAINTAIN MINIMALLY INVASIVE ACCESS FOR EXCHANGING INTERNAL BILIARY STENTS

[75] Inventor: Jonathan J. Trambert, Riverdale, N.Y.

[73] Assignee: Montefiore Hospital and Medical Center, Bronx, N.Y.

[21] Appl. No.: 891,721

[22] Filed: Jun. 25, 1992

[51] Int. Cl.⁵ ............................................ A61M 5/00
[52] U.S. Cl. .................................. 604/164; 604/175; 604/264; 606/108
[58] Field of Search ............... 604/8, 164, 174-175, 604/264, 280, 281; 606/108, 191, 198

[56] References Cited

U.S. PATENT DOCUMENTS

| 4,256,102 | 3/1981 | Monaco | 604/8 X |
|---|---|---|---|
| 4,392,855 | 7/1983 | Oreopoulos et al. | 604/175 |
| 4,511,356 | 4/1985 | Froning et al. | 604/164 |
| 4,593,687 | 6/1986 | Gray et al. | 604/164 X |
| 4,698,056 | 10/1987 | Ciannella | 604/164 |
| 4,699,611 | 10/1987 | Bowden | 604/51 |
| 4,758,219 | 7/1988 | Sacks et al. | 604/54 |
| 4,803,999 | 2/1989 | Liegner | 128/763 |
| 4,913,683 | 4/1990 | Gregory | 604/8 |
| 4,946,444 | 8/1990 | Heimke et al. | 604/175 |
| 5,084,024 | 1/1992 | Skinner | 604/175 |
| 5,098,397 | 3/1992 | Svensson et al. | 604/175 |
| 5,152,777 | 10/1992 | Goldberg et al. | 606/200 |

Primary Examiner—C. Fred Rosenbaum
Assistant Examiner—Corrine Maglione
Attorney, Agent, or Firm—Anthony J. Casella; Gerald E. Hespos

[57] ABSTRACT

A catheter is provided to maintain minimally invasive access for exchanging internal biliary stents. The catheter includes a catheter housing and a catheter obturator. The catheter housing includes an elongated hollow tube with an enlarged flange member at one end, and the diameter of the tube is sized such that a guidewire may pass through it, gaining access to an occluded internal biliary stent. The catheter obturator is used to seal off the hollow tube of the catheter housing for preventing any backflow of bile from occurring through the catheter lumen.

5 Claims, 8 Drawing Sheets

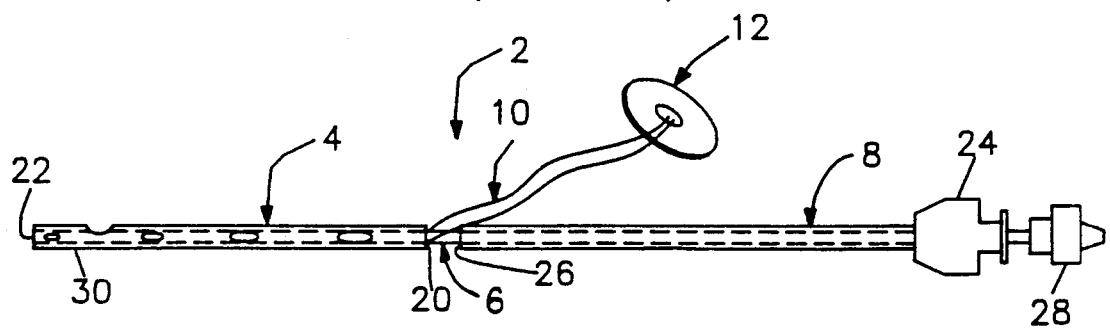
FIG. 1
(PRIOR ART)
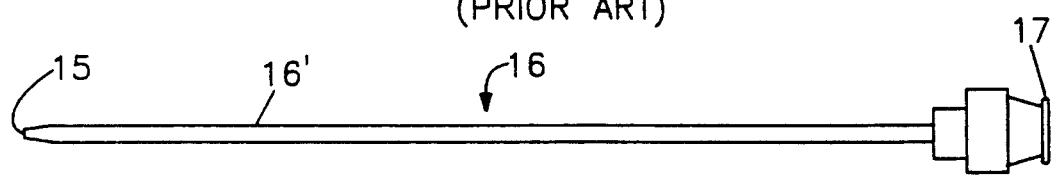
FIG. 2
(PRIOR ART)
FIG. 3
(PRIOR ART)
FIG. 4
(PRIOR ART)
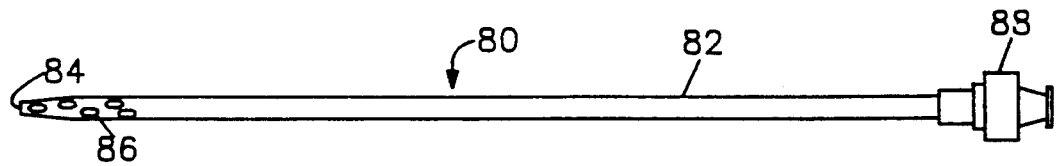
FIG. 5
(PRIOR ART)
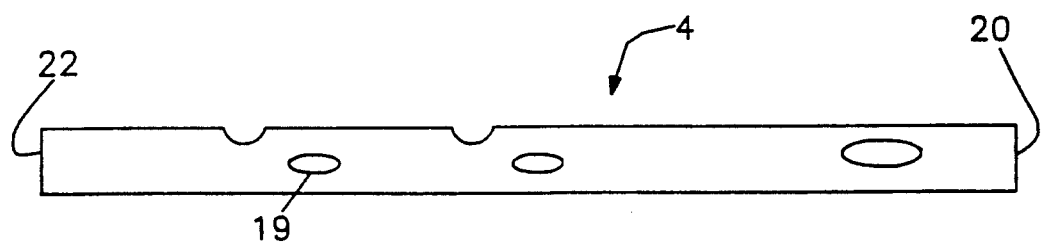

CATHETER TO MAINTAIN MINIMALLY INVASIVE ACCESS FOR EXCHANGING INTERNAL BILIARY STENTS

BACKGROUND OF THE INVENTION

Bile, a very bitter, alkaline, greenish-yellow to golden-brown fluid, is produced by the liver. Bile contains salts, cholesterol, lecithin, fat, various pigments and mucin. The bile secreted by the liver serves two main functions: to get rid of certain waste products and to aid in digestion by assisting in the emulsification and absorption of fats from the intestines. Normally, bile flows from glands in the liver into many tiny bile tributaries in the liver. These tributaries eventually join together to empty into a large bile duct known as the common bile duct. From the common bile duct, the bile flows into the duodenum, where it mixes with digesting food.

The bile duct provides for bile drainage between the liver and duodenum. The bile ducts, however, are prone to strictures. A stricture is the narrowing of the lumen (the space inside of a tube). A stricture in a bile duct prevents bile drainage between the liver and duodenum. The duodenum is the first part of the small intestine where the bile mixes with digesting food. When a patient has a malignant biliary stricture, the stricture may or may not be amenable to a surgical cure or bypass.

If the malignant biliary stricture is not amenable to a surgical cure or bypass, a palliative drainage procedure is required. A palliative drainage procedure is designed to prolong the life of the patient and to make the patient more comfortable when the condition of the patient is incurable. There are three principal palliative drainage options for patients with malignant biliary strictures.

The first option is external biliary drainage, in which a drainage catheter is inserted and extends percutaneously (through the skin) into the bile ducts above the stricture and functions to drain the bile externally into a bag. With external biliary drainage, a catheter, which is a hollow tube of rubber or plastic is inserted through a small hole in the skin and liver, for the purpose of discharging bile from the liver into a bag located external of the body.

The second palliative option is an external-internal stent. The external-internal stent has a percutaneous catheter extending through the biliary obstruction into the duodenum or jejunum (the portion of the small intestine extending between the duodenum and the lower portion of the small intestine), and can drain bile internally if the catheter is capped, or externally if the catheter is left uncapped. Therefore, the external-internal stent may either drain bile into a bag located externally to the body, or the external-internal stent may drain bile internally, into the duodenum or jejunum.

The third palliative option is a total internal stent. The latter is placed entirely within the liver across the biliary obstruction. All bile drainage is done internally between the liver and the duodenum. The stent is fully located internal of the body and no external access to the stent remains.

A total internal stent is usually preferable over an externally orientated stent, since the patient will not have a catheter protruding from his body, as it may tend to constantly remind him of an incurable condition. There is also less skin irritation and pain associated with the total internal stent, as externally orientated catheters are known to cause skin irritation and pain at the skin entry site. Also, there is less risk of bile bacterial colonization and cholangiolitis with an internal stent, as compared to an externally orientated stent. Cholangiolitis, which is the inflammation of the bile ducts within the liver, occurs occasionally with external orientated stents. Accordingly, it may be imperative to the patient that the usage of a total internal stent is to be the preferred palliative option.

The prior art internal stent apparatus is the CAREY-COONS TM soft stent biliary endoprosthesis kit, the manufacturer being Medi-Tech ® of Watertown, Mass. The Carey-Coons soft stent biliary endoprosthesis kit is primarily comprised of: an internal stent; a stabilizer; a straightener; a dilator; an initial external drainage catheter; a guidewire; and an anchor button.

The Carey-Coons endoprosthesis kit functions such that the straightener inserts into and passes through both the stabilizer and internal stent. These three components are assembled as a unit functioning to telescopically slide over a guidewire internal of the body. The nylon sutures and plastic anchor are attached to a proximal end of the internal stent. The plastic anchor button secures the internal stent within the body, preventing the stent's migration. The anchor button is placed into the subcutaneous tissues, thereafter the anchor button is covered by the skin.

The Carey-Coons internal stent is inserted within the liver either through an endoscope or through a percutaneous transhepatic approach. The endoscope approach is often less traumatic and painful as compared to the percutaneous transhepatic approach. Internal stents placed endoscopically usually can be exchanged endoscopically when they occlude. The internal stent tends to occlude usually within three months of placement. However, sometimes endoscopic internal stent placement or exchange is technically not possible. When endoscopic exchange of internal stents is not possible, re-access to the biliary tract must be accomplished through the percutaneous transhepatic approach. The percutaneous transhepatic approach, however, commits the patient to hospitalization and a potentially painful procedure every time their internal stent occludes.

The Carey-Coons internal stent, through a percutaneous transhepatic approach, is deployed across the stricture in the biliary duct. The first step of this procedure is the percutaneous transhepatic insertion of a guidewire through the hepatic duct of the liver and into the biliary duct, thereafter proceeding through the biliary duct stricture and into the duodenum. The Carey-Coons three piece assembled unit is then telescopically positioned over the guidewire and slipped over the guidewire until the stent is deployed across the stricture in the biliary duct.

The physician then disengages the straightener from the stabilizer, and thereafter the straightener is extracted externally from the body. The physician then removes the stabilizer so that it is extracted externally from the body. With the guidewire still in place, the initial external drainage catheter is telescopically positioned over the guidewire and advanced over the guidewire so that the tip of the initial external drainage catheter is deployed near the internal stent. The guidewire is then removed. Thus, the initial external drainage catheter enables both the biliary tree and internal stent to be flushed and drained, thus insuring that blood and debris which result from the manipulation in the liver will not clog the internal stent. After about two days the initial external drainage catheter is removed from the body.

Migration of the stent in the biliary duct is prevented by the nylon sutures attached to the proximal end of the internal stent. These sutures are attached to a plastic anchor button which is embedded by the physician in the subcutaneous tissue under the dermis layer of the skin.

When the Carey-Coons internal stent occludes, it first must be released from the sutures before it may be removed or exchanged. In order to remove the sutures, uncovering of the plastic button embedded in the subcutaneous tissue is required. The plastic button is uncovered through a subcutaneous cutdown, which serves to avail the plastic anchor button to the physician. The sutures attaching to the plastic anchor button embedded in the subcutaneous tissue are then severed, and the plastic anchor button is thereafter removed from the subcutaneous tissue. Next, access to the biliary duct can sometimes be accomplished by slipping a dilator telescopically over the nylon sutures, using the nylon suture essentially as a guidewire to the occluded stent. The dilator enlarges the cavity in the skin and liver which connect to the biliary duct. The occluded stent is then removed from the bile duct. The occluded stent may be removed either externally through the skin or it may be pushed into the bowel, thereafter passing out with the fecal stream. Lastly, a new guidewire is slipped through the dilator until it passes through the stricture in the biliary duct. The dilator is then removed from the body by telescopically sliding it over the guidewire until it is external of the body. A new three piece Carey-Coons assembled unit is then telescopically positioned over the guidewire and slipped over the guidewire until the internal stent lies across the stricture in the biliary duct. The process to prevent migration of the stent out of the bile ducts, as set forth above, is then repeated.

Not infrequently, however, the sutures may not be strong enough to guide a dilator into the internal organs of the patient. In such instances, a brand new percutaneous transhepatic access is needed, subjecting the patient to an additional multi-step, potentially painful procedure.

Hence, there exists a need to provide for a more efficient apparatus serving to simplify the removal and exchange of internal stents.

It is therefore a primary object of the subject invention to provide for a surgical apparatus functioning to simplify the removal and exchange of internal stents.

It is a further object of the subject invention to provide a surgical means for exchanging and removing internal stents without the requirement of having to form a new cavity from the external layer of the skin to the biliary duct.

A further object of the subject invention is to provide for an apparatus having a more efficient anchoring means for stabilizing the subject invention when it is within the internal organs of the human body.

SUMMARY OF THE INVENTION

The subject invention provides a catheter which allows for simpler and easier access to an internal stent within the biliary duct. The subject catheter is constructed from a biocompatible plastic material suitable for use in medical applications. The subject catheter includes a catheter housing having a unitary tubular elongated member having opposed ends, with one end being open ended and tapered, while the other end is formed with approximately a one centimeter diameter flange member. The tubular elongated member of the catheter housing is preferably circular. The plane of the enlarged flange member of the catheter housing is preferably perpendicular to the length of the tubular elongated member. The center of the enlarged flange member has a hole connecting to the tubular elongated member. The subject catheter additionally includes a catheter obturator which comprises a unitary solid elongated member having opposed ends, with one end integrated to a flange member. The solid elongated member is preferably circular and the plane of the flange member of the catheter obturator is preferably perpendicular to the length of the tubular elongated member.

In operation, the subject catheter is positioned internally within the body, providing easy access to an internal stent within the biliary duct. The subject catheter provides a pre-existing channel leading to the biliary duct, thereby providing an efficient means for percutaneous removal and exchange of internal stents.

The subject catheter may be utilized with elements of the Carey-Coons internal stent system such that, first, the physician percutaneously and transhepatically enters a bile duct with a needle. Next, a guidewire is inserted into the needle, passing through the bile duct in the liver, proceeding through the biliary ducts through the stricture and thereafter passing into the duodenum. The physician then telescopically advances a Carey-Coons internal biliary stent system, absent the nylon sutures and plastic anchor button, over the guidewire, until the internal biliary stent lies across the stricture within the biliary duct. The surgeon then removes the straightener and the stabilizer. The initial external drainage catheter is then inserted over the guidewire and the guidewire is then removed from the body. After approximately two days, or when it has been established that the internal stent has not clogged and is functioning well, the initial external drainage catheter is exchanged for the catheter of the subject invention. First, a guidewire is inserted into the initial external drainage catheter and slidably received through the initial external drainage catheter and proceeding into the internal biliary stent. The initial external drainage catheter is slidably retracted over the guidewire until it is external of the body. The physician then telescopically slides the subject tubular catheter housing over the guidewire such that the open tapered end of the catheter housing is either adjacent to the internal stent or is coaxially entering it. The enlarged flange member of the catheter housing is then embedded in the subcutaneous tissue. A removable plastic catheter obturator is then telescopically inserted into the hole on the enlarged flange member of the catheter housing, and inserted through the elongated tubular member, thereby preventing the backflow of bile to proceed from the elongated tubular member of the catheter housing to the subcutaneous tissue in which the enlarged flange member of the catheter housing is embedded. After the enlarged flange portion of the catheter housing is embedded in the subcutaneous tissue, the small incision made on the outer layer of the skin, will be sutured by the physician, so that the skin covers the enlarged flange member of the catheter housing as well as the flange member of the catheter obturator.

The enlarged flange member of the catheter housing functions to stabilize the position of the subject catheter and thus prevents it from migrating into the liver, thereby becoming inaccessible. For the next few months, the internal stent is positioned across the stricture in the biliary duct and operates to drain bile between the liver and the duodenum. The enlarged flange member of the catheter housing remains embedded in the subcutaneous tissue, while the elongated tubular member maintains an easily accessible channel leading to the internal stent in the biliary duct.

When the internal biliary stent fails or occludes, access to the internal stent for removal or exchange is accomplished through the catheter of the subject invention. First the physician performs a subcutaneous cutdown in the outer layer of the skin to uncover the enlarged flange member of the catheter housing. The catheter obturator is then telescopically removed from the catheter housing, thereby enabling a guidewire to be inserted into the hole of the enlarged flange member of the catheter housing. The guidewire is inserted through the tubular elongated member of the catheter housing and extends to the internal biliary stent, thereby allowing for easy removal and replacement of the failed internal stent. Thus, the subject catheter eliminates the need for a new invasive percutaneous transhepatic puncture for re-access to the bile ducts.

BRIEF DESCRIPTION OF THE DRAWINGS

FIG. 1 illustrates the components of the prior art internal biliary stent system;

FIG. 2 is a side elevational view of a dilator used with the prior art internal biliary stent system;

FIG. 3 is a side elevational view of a guidewire used with the prior art internal biliary stent system;

FIG. 4 is an elevational view of an initial external drainage catheter used with the prior art internal biliary stent system;

FIG. 5 is an elevational view of an internal biliary stent used with the prior art internal biliary stent system;

DETAILED DESCRIPTION OF THE PREFERRED EMBODIMENT

Figure 6:
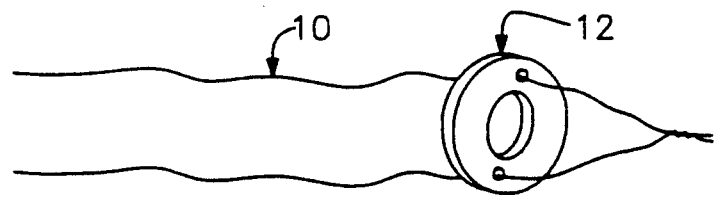
FIG. 6 is an elevational view of nylon sutures attached to a plastic anchor button of the prior art system.

As illustrated in FIG. 1, the prior art Carey-Coons internal biliary stent system 2 includes an internal biliary stent 4, a straightener 6, a stabilizer 8 and nylon sutures 10 attached to a plastic anchor button 12. The Carey-Coons internal biliary stent system 2 additionally includes a dilator 16 as shown in FIG. 2, a guidewire 14 as shown in FIG. 3, and an initial external drainage catheter 80 as shown in FIG. 4.

Figure 7:
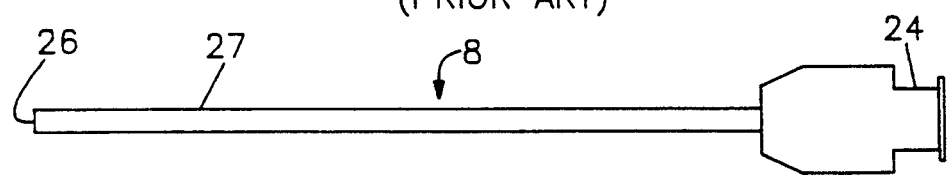
FIG. 7 is a side elevational view of a stabilizer used with the prior art internal biliary stent system.
Figure 8:
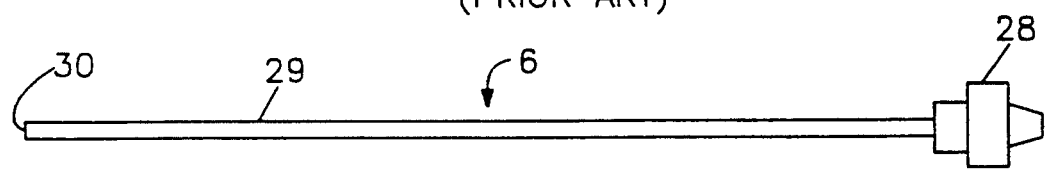
FIG. 8 is a side elevational view of a straightener used with the prior art internal biliary stent system.

As shown in FIG. 5, the internal biliary stent 4 includes an elongated tubular member with opposed open ended rearward 20 and forward ends 22. A plurality of spaced holes 19 are disposed along the length of the internal biliary stent 4 for facilitating proper drainage of bile. The Carey-Coons internal biliary stent 4 additionally includes nylon sutures 10, as illustrated in FIG. 6, with one end of the nylon sutures 10 being fastened to the rearward end 20 of the internal biliary stent 4, while the opposing ends of the nylon sutures 10 are attached to a plastic anchor button 12. The stabilizer 8, as illustrated in FIG. 7, includes an elongated tubular member 27 having an enlarged threaded open end 24 and an opposed open end 26. As illustrated in FIG. 8, the straightener 6 includes an elongated tubular member 29 having an enlarged threaded open end 28 and an opposed open end 30. The diameter of the tubular member 29 of straightener 6 is smaller than the diameter of tubular portion 27 of stabilizer 8 such that the straightener 6 is capable of being slidably received into both the stabilizer 8 and the internal biliary stent 4. The length of the elongated tubular member 29 of the straightener 6 is dimensioned such that the straightener 6 is capable of being slidably received through the tubular portion 27 of the stabilizer 8, with the open end 30 of the straightener 6 being disposed adjacent the open end 22 of the internal biliary stent 4, as shown in FIG. 1.

The dilator 16, as illustrated in FIG. 2, includes an elongated tubular member 16' having an opposing enlarged rearward end 17 and a forward tapered end 15. The guidewire 14, as illustrated in FIG. 3, is preferably constructed of a solid elongated metal wire. The diameter of the guidewire 14 is dimensioned such that the guidewire 14 may be slidably received into the straightener 6 and dilator 16. The initial external drainage 80 catheter, as shown in FIG. 4, includes an elongated tubular member 82 with a tapered end 84 and an opposed enlarged end 88. A plurality of holes 86 are disposed along the elongated tubular member 82 in close proximity to the open tapered end 84.

Figure 11:
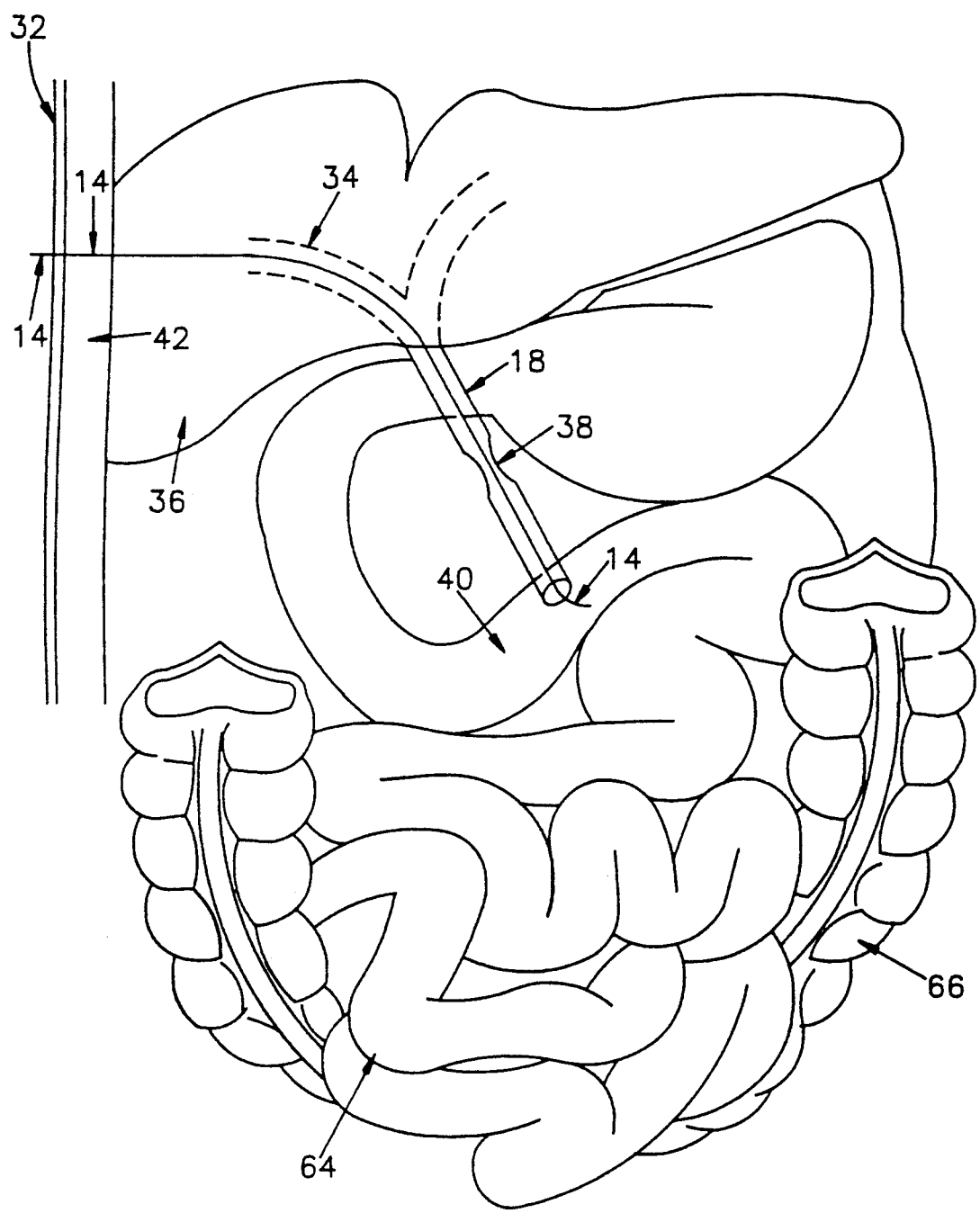
FIG. 11 is an elevational view of body parts shown with a guidewire being passed through the hepatic ducts in the liver through the bile duct stricture and into the duodenum.

FIG. 11 shows the intended environment for an internal biliary stent system, and illustrates a liver 36 having hepatic ducts 34 connecting to a biliary duct 18. The latter connects to a duodenum 40, and intermediate the length of the biliary duct 18 is a stricture 38. FIG. 11 also illustrates the outer layer of the skin 32, the subcutaneous tissue 42, and both the large intestine 64 and small intestine 66.

Figure 12:
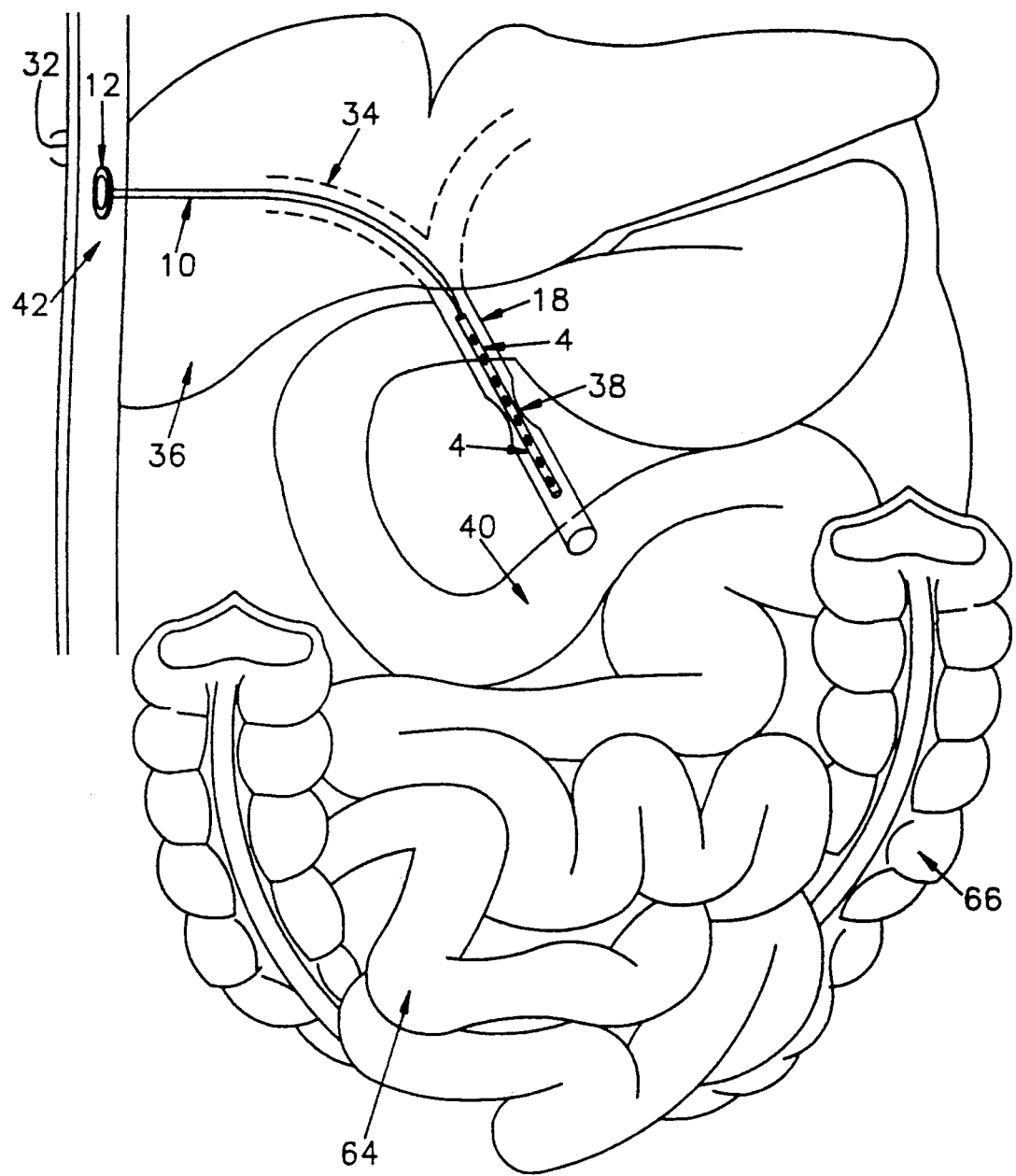
FIG. 12 is an elevational view of body parts with an internal biliary stent being deployed across the bile duct stricture having the prior art plastic button embedded in the subcutaneous tissue.

The surgical procedure for inserting the internal biliary stent 4 using the Carey-Coons internal stent system 2 (see FIG. 1) is first, the straightener 6 is slidably received into both the stabilizer 8 and the internal stent 4, with the threaded end 28 of the straightener 6 connected to the threaded end 24 of the stabilizer 8. Next, as illustrated in FIG. 11, through an incision in the skin, the surgeon telescopically inserts the guidewire 14 through the outer layer 32 of the skin and proceeding through a hepatic duct 34 in the liver 36 and further proceeding across the bile duct stricture 38 and into the duodenum 40. Turning to FIG. 12, the Carey-Coons internal biliary stent system 2 is telescopically slid over the guidewire 14, such that the internal stent 4 is disposed across the bile duct stricture 38. The straightener 6 is then disengaged with the stabilizer 8, and the straightener 6 is removed over the guidewire 14 until it is external of the outer layer of the skin 32. The surgeon then removes the stabilizer 8 over the guidewire 14 until it is external of the outer layer of the skin 32. With the guidewire 14 still in place, the initial external drainage catheter 80 is telescopically positioned over the guidewire 14 and advanced over the guidewire 14 such that the open tapered end 84 of the initial external drainage catheter 80 is placed adjacent to the internal biliary stent 4. The guidewire 14 is then removed. After approximately two days, the initial external drainage catheter 80 is extracted externally of the body. The plastic anchor button 12, which is attached to the internal stent 4 through the nylon sutures 10, is then positioned and embedded in the subcutaneous tissue 42, operating to prevent any future migration of the internal stent 4.

When the internal stent 4 occludes, the prior art plastic anchor button 12 embedded in the subcutaneous tissue 42 must be uncovered before the occluded internal stent 4 may be removed or exchanged. First, the physician makes an incision in the outer layer of the skin 32 to uncover the plastic anchor button 12. Next, the physician severs the nylon sutures 10 attached to the plastic anchor button 12. The plastic anchor button 12 is then removed from the subcutaneous tissue 42 and extracted out of the body. Next, access to the occluded internal biliary stent 4 in the biliary duct 18 can be attempted by slipping the dilator 16 telescopically over the nylon sutures 10, such that the nylon sutures 10 function as a guidewire and slidably receive the dilator 16. Thereafter, a series of dilators 16 of gradually increasing diameter form an enlarged cavity leading to the biliary duct 18, thus allowing for the occluded internal biliary stent 4 to be either extracted through the enlarged cavity or the occluded internal biliary stent 4 may be pushed into the bowel, causing the occluded internal biliary stent 4 to exit the body through the fecal stream. A guidewire 14 is then telescopically inserted and slipped through the rearward end 17 of the dilator 16 such that the guidewire 14 passes through the forward tapered end 15 of the dilator 16 and proceeds into the duodenum 40. The dilator 16 is then extracted from the body by telescopically sliding the dilator 16 over the guidewire 14 until the dilator 16 is fully external of the body, leaving the guidewire 14 within the body, as illustrated in FIG. 11. The process for inserting a new internal stent 4 is then repeated, in the steps detailed above.

Figure 9:
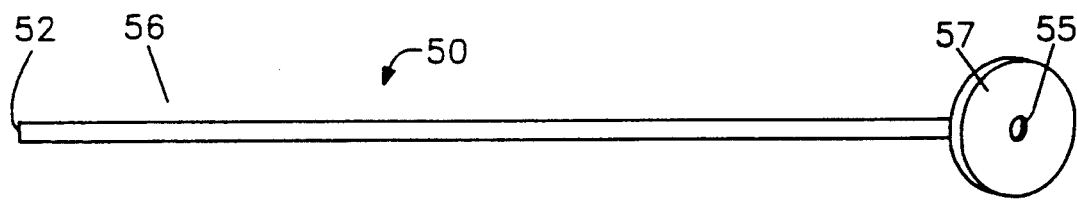
FIG. 9 is a perspective view of a catheter housing forming a portion of the subject invention.
Figure 10:
FIG. 10 is a side elevational view of a catheter obturator forming a portion of the subject invention.

Turning to FIGS. 9 and 10, the catheter of the subject invention includes both a catheter housing 50 and a catheter obturator 58. The subject catheter is used with: the internal biliary stent 4 as shown in FIG. 5; the stabilizer 8 as shown in FIG. 7; the straightener 6 as shown in FIG. 8; the initial external drainage catheter as shown in FIG. 4; the dilator 16 as shown in FIG. 2; and the guidewire 14 as shown in FIG. 3. The catheter housing 50 and obturator 58 are constructed from a biocompatible plastic material suitable for use in medical applications. The catheter housing 50 comprises a unitary tubular elongated member 56 having an open end 52 and an enlarged flange member 57 at its opposed end. The tubular elongated member 56 of the catheter housing 50 is preferably circular, with the plane of the enlarged disc-shaped flange member 57 being preferably perpendicular to the length of the tubular elongated member 56. The enlarged flange member 57 has a central hole 55, and is formed unitary with the tubular member 56.

As shown in FIG. 10, the catheter obturator 58 comprises a unitary solid elongated member 59 including a closed end 60 and flange member 63 at its opposed end. The diameter of the solid elongated member 59 is slightly smaller than the diameter of the central opening in the tubular member 56 so as to be slidably received into the catheter housing 50, and so as to effectively plug the lumen of the subject catheter, thereby preventing bile backflow to the subcutaneous tissues.

Figure 13:
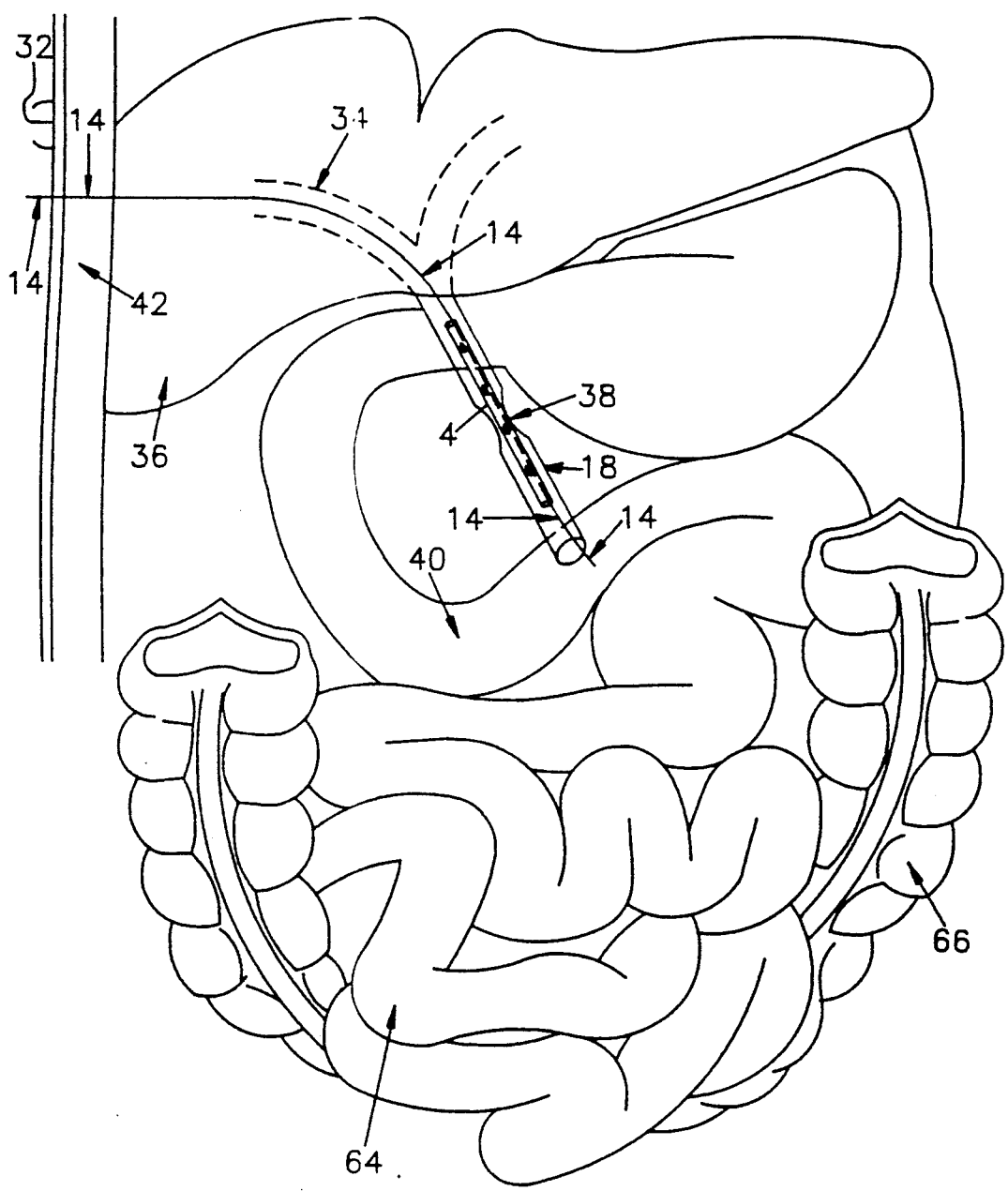
FIG. 13 is an elevational view of body parts with an internal biliary stent being deployed across the biliary duct stricture with a guidewire passing therethrough.

The surgical procedure to insert the internal stent 4 utilizing the subject catheter will now be described with reference to FIGS. 13–16. As illustrated in FIG. 13, the physician first enters a bile duct 18 through the skin and liver substance with a needle through which the physician telescopically inserts the guidewire 14 into the hepatic duct 34, proceeding through the bile duct stricture 38 and into the duodenum 40. The internal biliary stent 4 is then telescopically inserted over the guidewire 14 and subsequently slipped over the guidewire 14 until it is positioned across the stricture 38 in the biliary duct 18, as shown in FIG. 13.

Figure 14:
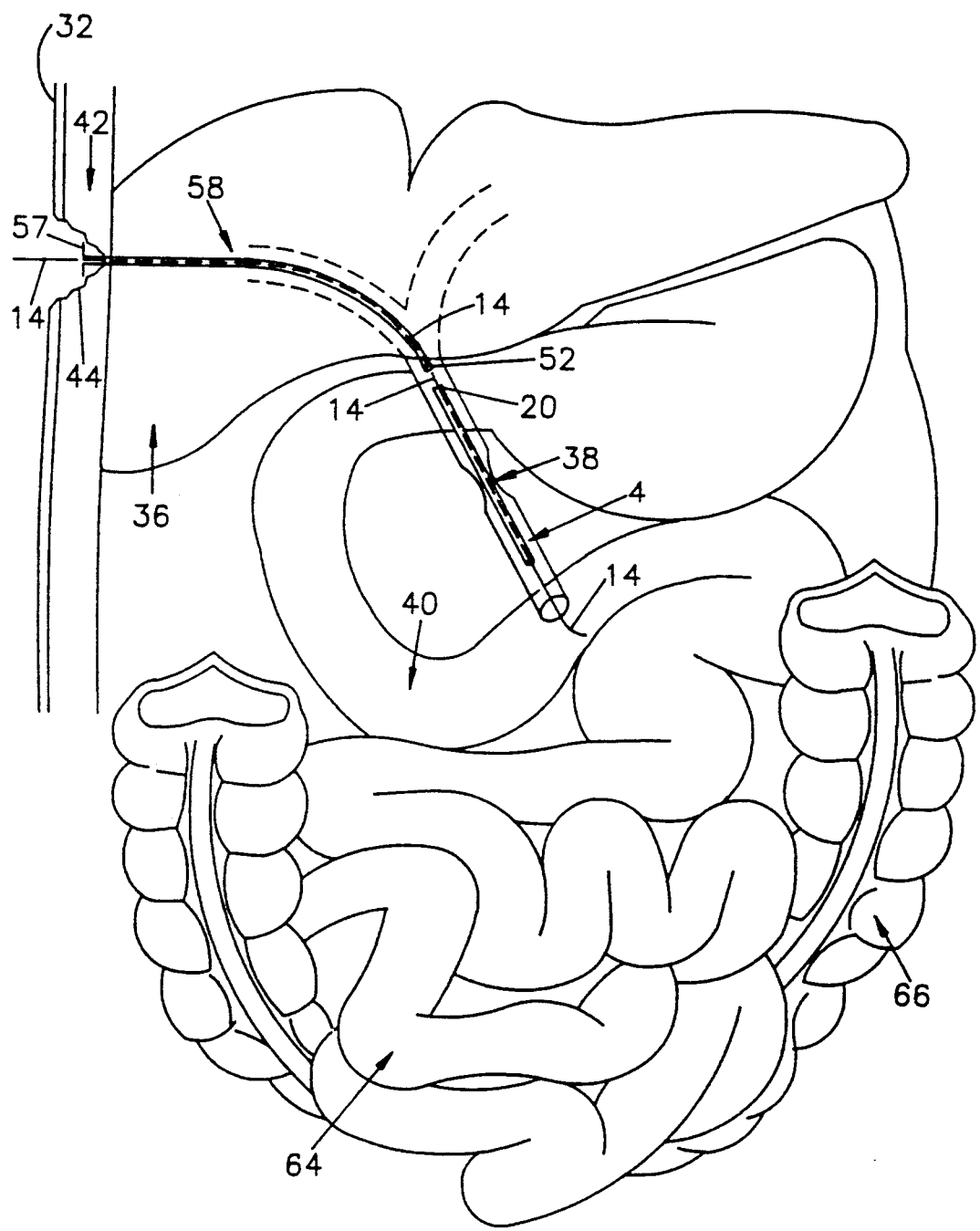
FIG. 14 is an elevational view of body parts with the catheter of the subject invention and an internal biliary stent with a guidewire passing therethrough.
Figure 15:
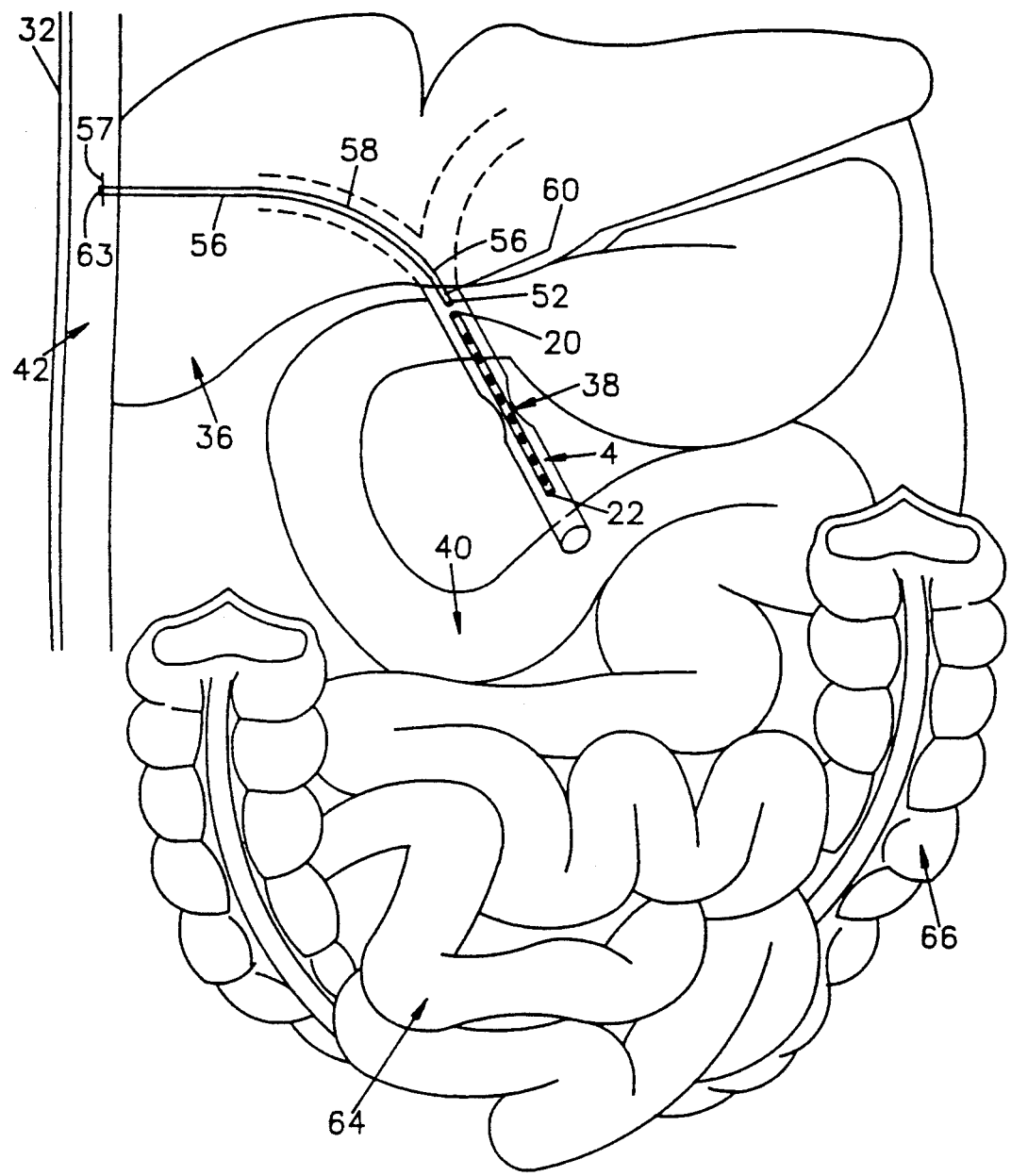
FIG. 15 is an elevational view of body parts with the catheter housing of the subject invention wherein the catheter obturator is placed thereinto, and of an internal biliary stent deployed across the bile duct stricture.

Turning to FIG. 14, the catheter housing 50 is then telescopically inserted over the guidewire 14 and subsequently slipped across the guidewire 14 until the open end 52 of the catheter housing 50 is either inserted into the rearward open end 20 of the internal stent 4 or the open end 52 of the catheter housing 50 is in close proximity to the rearward end 20 of the internal biliary stent 4. The enlarged flange member 57 of the catheter housing is then embedded in the subcutaneous tissue 42 through a subcutaneous cutdown 44. Next, as illustrated in FIG. 15, the guidewire 14 is telescopically extracted from both the internal stent 4 and catheter housing 50 until the guidewire 14 is located entirely external of the outer layer of skin 32. Next, the closed end 60 of the catheter obturator 58 is telescopically inserted into the hole in the enlarged flange member 57 of the catheter housing 50 such that the flange member 63 of the catheter obturator is adjacent to the enlarged flange member 57 of the catheter housing 50. The physician then sutures the subcutaneous cutdown 44 over the enlarged flange member 57 of the catheter housing 50. Thereafter, the subject catheter 50 maintains a channel leading to the biliary duct 18 with minimum discomfort to the patient.

Figure 16:
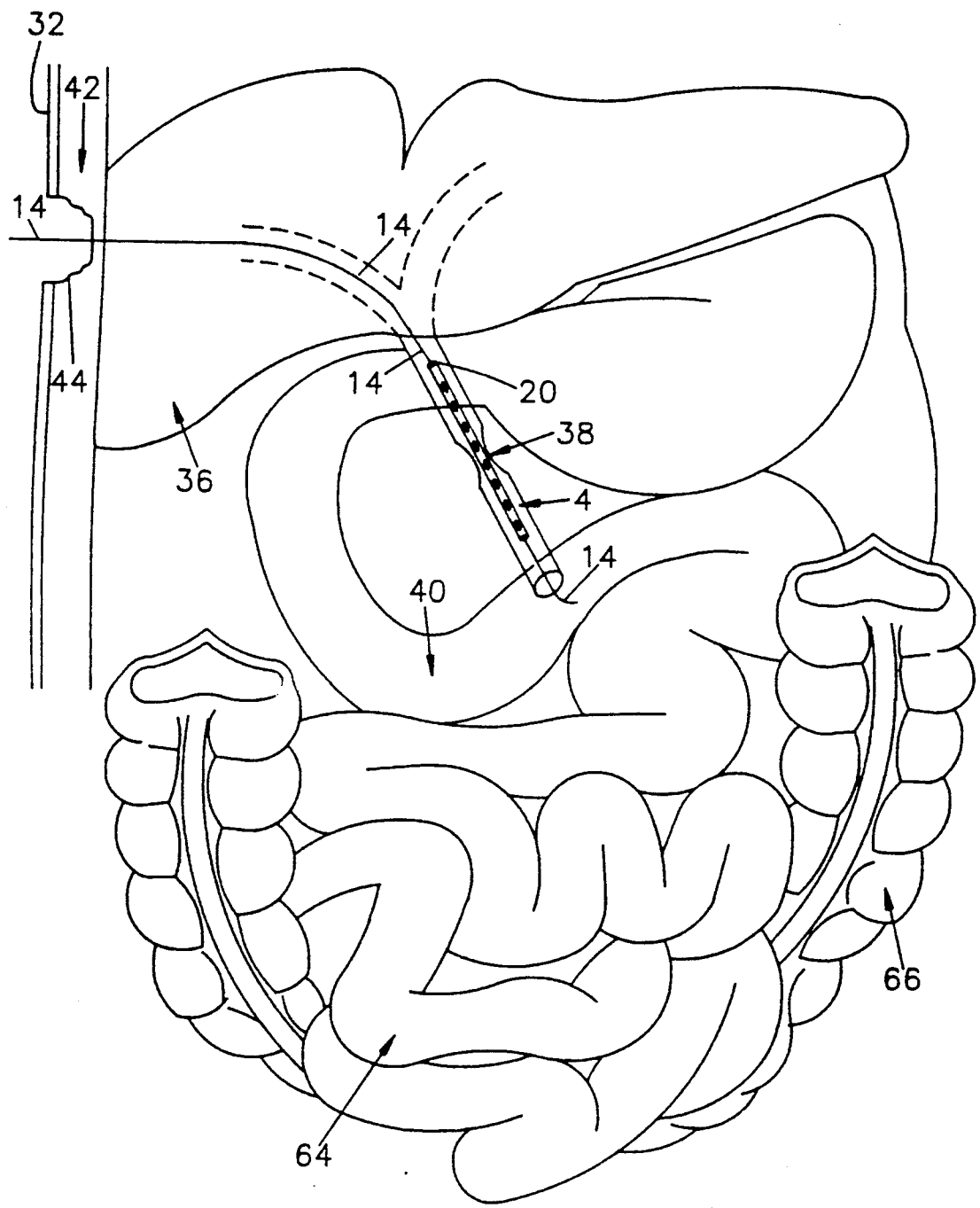
FIG. 16 is an elevational view of body parts of an internal biliary stent being deployed across the biliary duct stricture with a guidewire passing therethrough.

When the internal biliary stent 4 occludes, it is necessary to exchange the internal biliary stent 4. The physician, as shown in FIG. 16, uncovers the enlarged flange member 57 of the catheter housing 50 in the subcutaneous tissue 42 through a subcutaneous cutdown 44. Next, the catheter obturator 58 is telescopically extracted from the catheter housing 50. A guidewire 14 is then telescopically inserted into the hole 55 in the enlarged flange member 57 of the catheter housing 50, the guidewire 14 is then slipped through the catheter housing 50 and into the biliary duct 38, proceeding through the occluded internal biliary stent 4. The catheter housing 50 is then telescopically extracted external of the body over the guidewire 14.

Removal of the occluded internal biliary stent 4 is thereafter carried out, as previously explained above. Similarly, the surgical procedure for the insertion of a new internal biliary stent 4, with the subject catheter 50, is repeated in the process detailed above.

While the invention has been described with respect to certain preferred embodiments, it is apparent that various changes can be made without departing from the spirit and scope of the invention as defined by the appended claims. For example, it is anticipated that the subject catheter may be useful in maintaining and servicing other types of biliary stents, including expandable metal stents.

I claim:

1. An internal biliary stent system including an internal biliary stent having an elongated tubular member having a plurality of spaced holes therein; a stabilizer having an elongated tubular member having an enlarged threaded portion at one end; a straightener including an elongated tubular member provided with an enlarged threaded portion at one end thereof and adapted to threadingly engage said enlarged threaded portion of said stabilizer, the diameter of said elongated tubular member of said straightener being smaller than the diameter of both the internal biliary stent and the tubular portion of said stabilizer such that said straightener may be slidably received into both said internal biliary stent and said stabilizer, said internal biliary stent system further including a guidewire of a diameter dimensioned to be slidably received within said tubular member of the straightener; a dilator having an elongated tubular member including an enlarged portion at one end; the improvement comprising: a catheter means for providing an access channel in the body while an internal biliary stent is disposed across a biliary stricture in a biliary duct, said catheter means including a catheter housing and a catheter obturator, said catheter housing having an elongated tubular member formed unitary with an enlarged flange member disposed at one end thereof, said elongated tubular member having a central opening extending therethrough, the plane of said enlarged flange member being disposed at an angle to the longitudinal axis of said elongated tubular member, said enlarged flange member including a central hole aligned with the central opening of said elongated tubular member, said catheter obturator comprising a unitary solid elongated member with a flange member disposed at one end thereof, with said solid elongated member of said catheter obturator being dimensioned to be slidably received into the tubular member of said catheter housing whereby, through a small incision in the skin, a guidewire together with said stabilizer and straightener function to insert an internal stent across a biliary stricture in a biliary duct, thereafterwards said stabilizer and straightener may be extracted externally of the body, said catheter housing then slidably passed over said guidewire such that the open end of said catheter housing is either adjacent to said internal stent or coaxially enters said stent, said guidewire being then extracted externally of the body, and said catheter obturator may be slidably received into said catheter housing such that said flange member of said catheter obturator is disposed adjacent said enlarged flange member of said catheter housing, thereafterwards the small incision may be sutured closed, and said catheter means thus functions to provide said access channel from the subcutaneous tissues to the bile duct to facilitate subsequent servicing of the stent.

2. An internal biliary stent system as in claim 1, wherein the catheter housing and the catheter obturator of the catheter means are constructed of a plastic material.

3. An internal biliary stent system as in claim 1, wherein the flange member of the catheter obturator is smaller than the enlarged flange member of the catheter housing.

4. An internal biliary stent system as in claim 1, wherein the flange member of the catheter obturator is circular.

5. An internal biliary stent system as in claim 1, wherein the enlarged flange portion of the catheter housing is circular.

* * * * *